United States Patent [19]

Gualtieri

[11] Patent Number: 5,479,375
[45] Date of Patent: Dec. 26, 1995

[54] REAL TIME IMAGING OF ACOUSTIC WAVE DEVICES

[75] Inventor: John G. Gualtieri, Oceanport, N.J.

[73] Assignee: The United States of America as represented by the Secretary of the Army, Washington, D.C.

[21] Appl. No.: 336,329

[22] Filed: Nov. 3, 1994

[51] Int. Cl.$^6$ ............................ G01N 29/00; G01B 9/00
[52] U.S. Cl. .................................................................. 367/7
[58] Field of Search ..................... 367/7, 11; 356/352, 356/372; 73/597, 643, 655

[56] References Cited

U.S. PATENT DOCUMENTS

| | | | |
|---|---|---|---|
| 3,706,965 | 12/1972 | Korpel | 367/7 |
| 5,042,302 | 8/1991 | Soelkner | 73/597 |
| 5,402,235 | 3/1995 | Monchalin | 356/352 |

OTHER PUBLICATIONS

Zuliani et al., "Probing of surface acoustic wave devices with large-diameter laser beam," J. Appl. Phys., vol. 44, pp. 2964–2970, Jul. 1973.
Soffer et al., "An Optical Imaging Method for Direct Observation and Study of Acoustic Surface Waves," Appl. Phys. Lett., vol. 15, pp. 339–342, Nov. 1969.
Zuliani et al., "Visualization of Acoustic Radiation in LiNbO$_3$," Phys. Lett., vol. 38A, pp. 87–88, Jan. 1972.
Ristic et al., "Probing of acoustic shear wave radiation in surface wave devices," Appl. Phys. Lett., vol. 21, pp. 85–87, Aug. 1972.
Alippi et al., "Acoustic-optics with surface acoustic waves—Devices and applications," Optica Acta, vol. 27, pp. 1061–1076, 1980.
Zory et al., "Light Diffraction Efficiency of Acoustic Surface Waves," Applied Optics, vol. 10, No. 9, pp. 2104–2106, Sep. 1971.

Primary Examiner—Daniel T. Pihulic
Attorney, Agent, or Firm—Michael Zelenka; William H. Anderson

[57] ABSTRACT

An acoustic wave imaging system comprises a prism for mounting to the back surface of a piezoelectric substrate of an acoustic wave device. The piezoelectric substrate comprises a front surface on which metallic interdigitated input and output transducers mount for generating acoustic waves on or below the front surface. An electric signal source connects to the input transducer while a load connects to the output transducer. The device may also include spaced metallic reflectors. A large laser beam propagates through an entrance face of the prism, passes through the back surface of the piezoelectric crystal and internally reflects off the front surface of the piezoelectric crystal. The laser beam diffracts into a number of components due to the creation of periodic surface corrugations and or periodic refractive index perturbations beneath the surface, which are caused by the acoustic waves. The beam components exit the prism and are focused by a lens onto its image plane. A spatial filter located at the focal plane of the lens blocks unwanted or undiffracted beam components while passing a diffracted component onto the image plane where it is detected by a charge coupled array device for real-time display, using a frame grabber and a computer to generate the display.

16 Claims, 2 Drawing Sheets

REAL TIME IMAGING OF ACOUSTIC WAVE DEVICES

GOVERNMENT INTEREST

The invention described herein may be manufactured, used and licensed by or for the Government for governmental purposes without the payment to me of any royalties thereon.

BACKGROUND OF THE INVENTION

1. Field of the Invention

This invention relates in general to the field of acoustic wave devices. More particularly, the invention relates to techniques particularly suitable for real-time imaging of acoustic wave devices having low electromechanical coupling efficiencies.

2. Description of the Prior Art

Acoustic wave devices typically include a rigid solid in which acoustic waves are made to propagate. These devices have been used in numerous conventional electronic systems as resonators, filters, delay lines and signal generators.

A surface acoustic wave (SAW) device, which is a common type of acoustic wave device, generally comprises a piezoelectric substrate with a polished surface on which surface acoustic waves are made to propagate. A metallic input transducer, which is connected to a source of electromagnetic energy, and a metallic output transducer, which is connected to a load, mount on the polished surface. Through a well known electromechanical coupling process, the input transducer launches the surface acoustic wave. The output transducer converts energy from the surface acoustic wave into electrical energy to drive the load.

A surface transverse wave (STW) device employs acoustic waves that propagate typically between two and ten acoustic wavelengths beneath the substrate surface. A conventional STW device is constructed similar to a SAW device and generally operates in a similar manner. However, the acoustic waves in a STW device propagate beneath the surface rather than on the surface as in a SAW device. Also in a STW device, the substrate is cut at a different angle and a metal layer is deposited on the substrate surface in the area between the input and output transducers to help restrict the acoustic wave propagation within two to ten acoustic wavelengths beneath the metal layer and the substrate surface.

In a SAW device, angstrom-sized surface acoustic waves are manifested by periodic particle motions which are essentially perpendicular to the substrate surface. These periodic particle motions create corrugations of the piezoelectric surface. In a STW device, the acoustic waves propagate beneath the substrate surface and the periodic particle motions are parallel or transverse to that surface. As such, surface corrugations are usually not found on a STW device. However, the transverse particle motions in a STW device normally create a periodic perturbation of the refractive index of the substrate which sets up a photoelastic strain grating.

During design and fabrication of acoustic wave devices, it has been the general practice to employ optical imaging techniques for direct observation and study of the effects of the acoustic waves on the piezoelectric substrate. Particularly, lasers are often used to scatter light energy from the piezoelectric substrate of an operating acoustic wave device. The laser light diffracts as it encounters the surface corrugations in a SAW device or the photoelastic strain grating in a STW device. Images of the diffracted light are later observed and studied to help designers improve the overall efficiency of such devices.

Those concerned with the development of acoustic wave devices, particularly those devices with low electromechanical coupling efficiencies, have long recognized the need for improved optical imaging systems and techniques. Ideally, an improved imaging system would have a high efficiency, would be low in cost, would have high reliability, and would be operable with inexpensive, low-power lasers, such as conventional helium-neon (HeNe) lasers as opposed to the current use of expensive, less manageable argon lasers. The present invention fulfills this need.

SUMMARY OF THE INVENTION

The general purpose of this invention is to provide a method and an apparatus for performing real-time imaging of acoustic wave devices. To attain this, the present invention contemplates a unique imaging apparatus and method that performs total internal reflection of a collimated light beam from the active region of an acoustic wave device. Acoustic waves in the active regions diffract the beam into several components, one of which is detected and displayed in real time as a three-dimensional image.

In general, the imaging apparatus of the present invention comprises a device having a member with a back surface and a front surface capable of supporting acoustic waves. An optical structure directs a collimated beam of light into the member through the back surface and incident on the front surface at an angle larger than the critical angle of the member to cause substantially total internal reflection of the collimated beam of light by the front surface. Acoustic waves are launched on or beneath the front surface for diffracting the beam of light into a plurality of components upon total internal reflection of the beam. A focusing structure focuses at least one of the components onto its image plane. A display located at the image plane generates real-time images of components focused at the image plane.

The method broadly comprises mounting a device having a member with a back surface and a front surface capable of supporting acoustic waves. A collimated beam of light is directed into the member through the back surface and incident with the front surface at an angle larger than the critical angle of the member to cause substantially total internal reflection of the collimated beam of light by the front surface. Acoustic waves launched in the member diffract the beam of light into a plurality of components upon total internal reflection of the beam. At least one of the components is focused onto the image plane and real-time images are generated of the focused components.

More specifically, the invention includes an acoustic wave imaging system having a prism which contacts the back surface of a piezoelectric substrate of an acoustic wave device. The piezoelectric substrate comprises a polished front surface on which metallic interdigitated input and output transducers mount. An electric signal source connects to the input transducer while a load connects to the output transducer. The acoustic wave device may also include one or more metallic reflectors on its front surface. A laser directs a large beam through an entrance face of the prism toward the front surface. The laser beam passes through the back surface of the substrate and undergoes total internal reflection off its front surface while being diffracted into a number of beam components by the acoustic waves. The beam components exit the prism and pass through a focusing lens. A spatial filter located at the focal plane of the lens blocks unwanted beam components while passing a diffracted component to the image plane where a CCD array, frame grabber and a computer display provide a real-time image.

As will become evident from the following description, the present invention has application in acoustic field diagnostics, image scanners and processors, and real-time signal processing operations, such as convolution, correlation, and spectrum analysis.

BRIEF DESCRIPTION OF THE DRAWINGS

Other objects, features, details, advantages and applications of the invention will become apparent in light of the ensuing detailed disclosure, and particularly in light of the drawings wherein.

DETAILED DESCRIPTION OF THE PREFERRED EMBODIMENT

Figure 1:
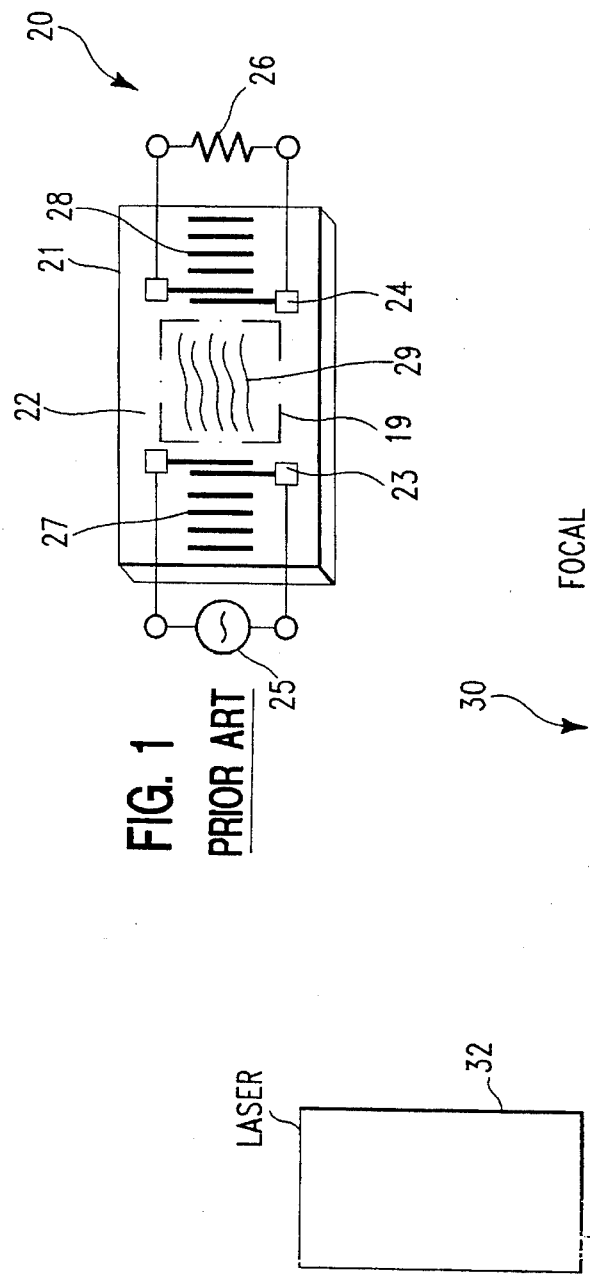
FIG. 1 is a schematic pictorial representation of a prior art SAW/STW device configured to operate as a SAW/STW resonator.

Referring now to the drawings, FIG. 1 shows a conventional acoustic wave resonator 20 formed from a piezoelectric substrate 21 with a polished front surface 22 on which are deposited metallic interdigitated input transducer 23 and output transducer 24. Electric signal source 25 connects to interdigitated input transducer 23. Load 26 connects to interdigitated output transducer 24. Two spaced sets of metallic reflectors 27 and 28 form resonant cavity 29 for supporting resonant standing acoustic waves. Piezoelectric substrate 21 may be formed from a conventional quartz crystal, which typically has a low electromechanical coupling efficiency.

Through a well known electromechanical coupling process, input transducer 23 launches an acoustic wave that propagates on front surface 22. FIG. 1 depicts the launched acoustic wave with wavy lines located in resonant cavity 29. Initially, the launched acoustic waves propagate from input transducer 23 toward reflector 28 and output transducer 24. Output transducer 24 extracts some of the energy in the acoustic wave while reflector 28 reflects a portion back toward reflector 27, which again reflects the acoustic wave back on itself. As this process continues, the reflected waves eventually create the standing acoustic waves in resonant cavity 29 while output transducer 24 extracts energy that drives load 26.

As discussed above, during design and fabrication of acoustic wave devices, such as resonator 20, it has been the general practice to employ optical imaging systems to observe and study the acoustic waves. Such imaging systems typically scatter light energy from the region of cavity 29. After the light is diffracted by the acoustic waves, images of the diffracted light are observed and studied by designers of such acoustic wave devices.

In the case of a SAW resonator, resonant cavity 29 would be located on surface 22 and the acoustic energy would be in the form of surface acoustic waves. As discussed above, a STW resonator often appears similar to a SAW resonator. However, the resonant cavity in a STW resonator would be just beneath surface 22 on which a metal layer is deposited.

To show a typical STW resonator, therefore, resonator 20 in FIG. 1 includes metal layer 19 which is depicted with phantom lines. Metal layer 19 resides on surface 22 in the area between transducers 23 and 24.

As is well known by those skilled in these arts, substrate 21 acts as an acoustic waveguide and transverse mode guidance occurs in both SAW and STW devices because the acoustic waves are reflected by impedance discontinuities from boundary edges. Multiple reflections from parallel boundary edges result in a discrete mode spectrum for the acoustic waveguide. It is these transverse modes that are imaged by the present invention.

Figure 2:
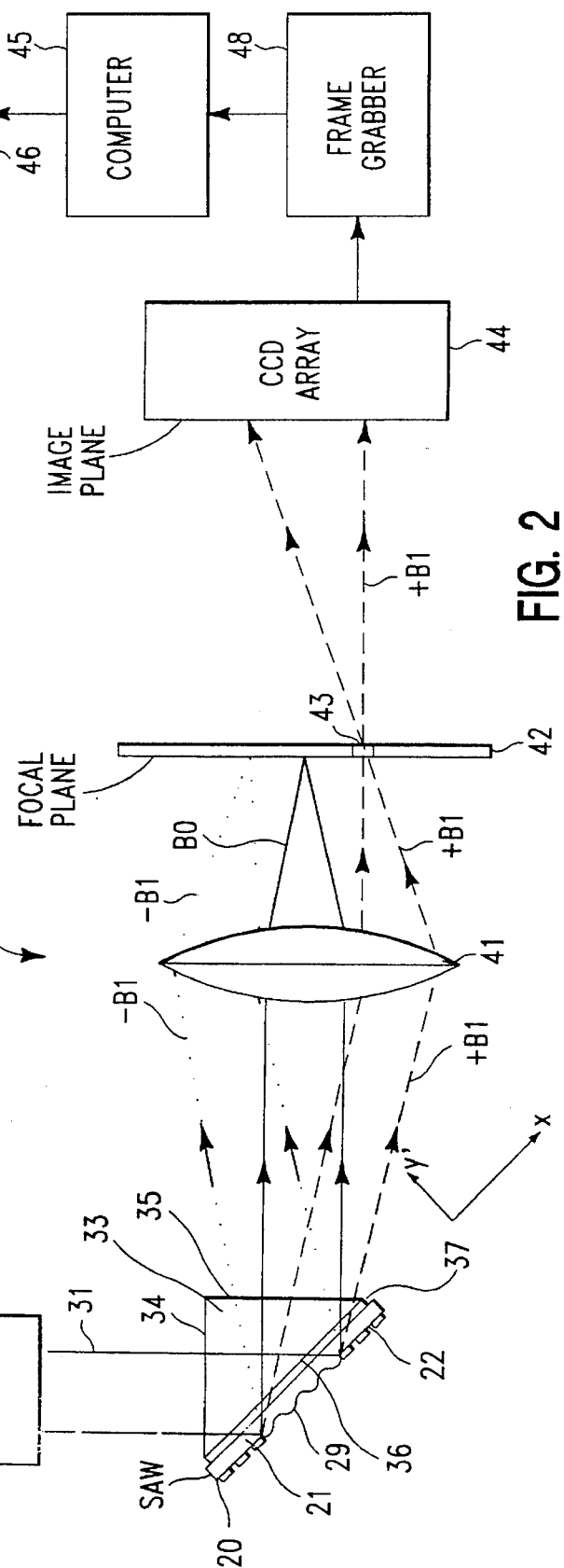
FIG. 2 is a schematic representation of a side elevation of a preferred embodiment of the invention.

FIG. 2, which depicts the preferred embodiment, shows resonator 20 positioned in optical imaging system 30. For illustrative purposes, the plane of FIG. 2 corresponds to the xy'-plane of a y-cut quartz crystal. In this regard, front surface 22 corresponds to the xz'-plane of the y-cut quartz crystal which corresponds to the X1–X2 plane of FIG. 3, to be described below in detail. Incident output beam 31 of large-beam laser 32 illuminates resonator 20 at an angle greater than its critical angle, thereby obtaining total internal reflection of beam 31 at front surface 22. A conventional low-cost, twenty milliwatt, helium-neon (HeNe) laser with a beam expander and collimator may be used to implement laser 32.

Right-angle optical prism 33 contacts the back surface of resonator 20 on the prism's transverse face 36 which together with the prism's entrance face 34 and exit face 35 form a forty-five degree right triangle. As such, front surface 22 is positioned to face away from prism 33. The back surface of piezoelectric substrate 21, i.e., the side opposite front surface 22, and transverse face 36 sandwiches refractive index matching fluid 37 to reduce interfacial reflections from prism 33 or substrate 21. Laser beam 31 enters prism 33 substantially normal to the prism's entrance face 34 and travels through prism 33, fluid 37 and substrate 21 where it is reflected by front surface 22 and diffracted in a manner to be described below in detail.

An entrance face of focusing lens 41 faces prism 33 such that lens 41 is oriented with its optic axis perpendicular to the prism's exit face 35. The exit face of lens 41 faces spatial filter 42, which is positioned at the focal plane of lens 41. Spatial filter 42 comprises an opaque surface with an opening 43. A charge coupled device (CCD) detector array 44, or other image detector, mounts at the image plane of lens 41 and connects to frame grabber 48. The output of frame grabber 48 connects to computer 45 which drives a display 46, such as a display monitor, a printer or a plotter.

As described above, coherent laser light from the expanded and collimated output beam 31 is incident on front surface 22 from inside piezoelectric substrate 21 at an angle greater than the critical angle for piezoelectric substrate 21. For the FIG. 2 example, beam 31 is made to travel at approximately a forty-five degree angle with respect to the y' axis, i.e., an axis normal to front surface 22, because the critical angle for a piezoelectric substrate made from quartz is approximately forty degrees with respect to the y' axis. Consequently, this orientation of laser beam 31 with respect to resonator 20 assures total internal reflection of laser beam 31 by front surface 22.

Additionally, because front surface 22 for a SAW device is physically distorted by acoustic waves propagating thereon, front surface 22 will act as a diffraction grating, causing beam 31 to be diffracted as it is totally reflected therefrom. Depending on the periodicity of the acoustic waves and the frequency of laser beam 31, constructive interference of the reflected light will occur along certain angles, thereby producing a limited number of diffracted beam components in addition to an undiffracted beam component.

More specifically, diffraction of laser beam 31 occurs primarily because of the acoustically created grating on front surface 22. In the STW case, the acoustic disturbance slightly penetrates front surface 22, periodically perturbing the refractive index of substrate 21, which causes a photo-elastic strain grating that leads to weak diffraction of laser beam 31. In the Raman-Nath limit for both SAW and STW devices, the three strongest components of light exiting prism 33 at exit face 35 will be the undiffracted component B0 and two first-order diffracted components +B1 and −B1, depicted as solid, dashed and dotted lines, respectively, in FIG. 2.

Lens 41 focuses components B0, +B1 and −B1 into small points at its focal plane. In one particular application, a 20.3 centimeter focal length f/2.9 lens was used to focus components B0, +B1 and −B1 onto the focal plane. Spatial filter 42, located at the focal plane, serves to block undiffracted component B0 and first-order component −B1 while allowing first-order component +B1 to pass to the image plane and be focused on CCD detector array 44. Array 44, which is a two-dimensional pixel array of CCD's, interfaces with frame grabber 48 which provides computer 45 with signals related to the intensity of component +B1 as detected at each pixel location. Computer 45 responds to inputs from frame grabber 48 and array 44 by displaying three-dimensional, real-time images of component +B1. These real-time images correspond to the intensity function of the SAW (or STW) mode along with recognizable features of the elements of resonator 20. As is well known, this intensity function will be proportional to the acoustic power as it is distributed on or below front surface 22.

Figure 3:
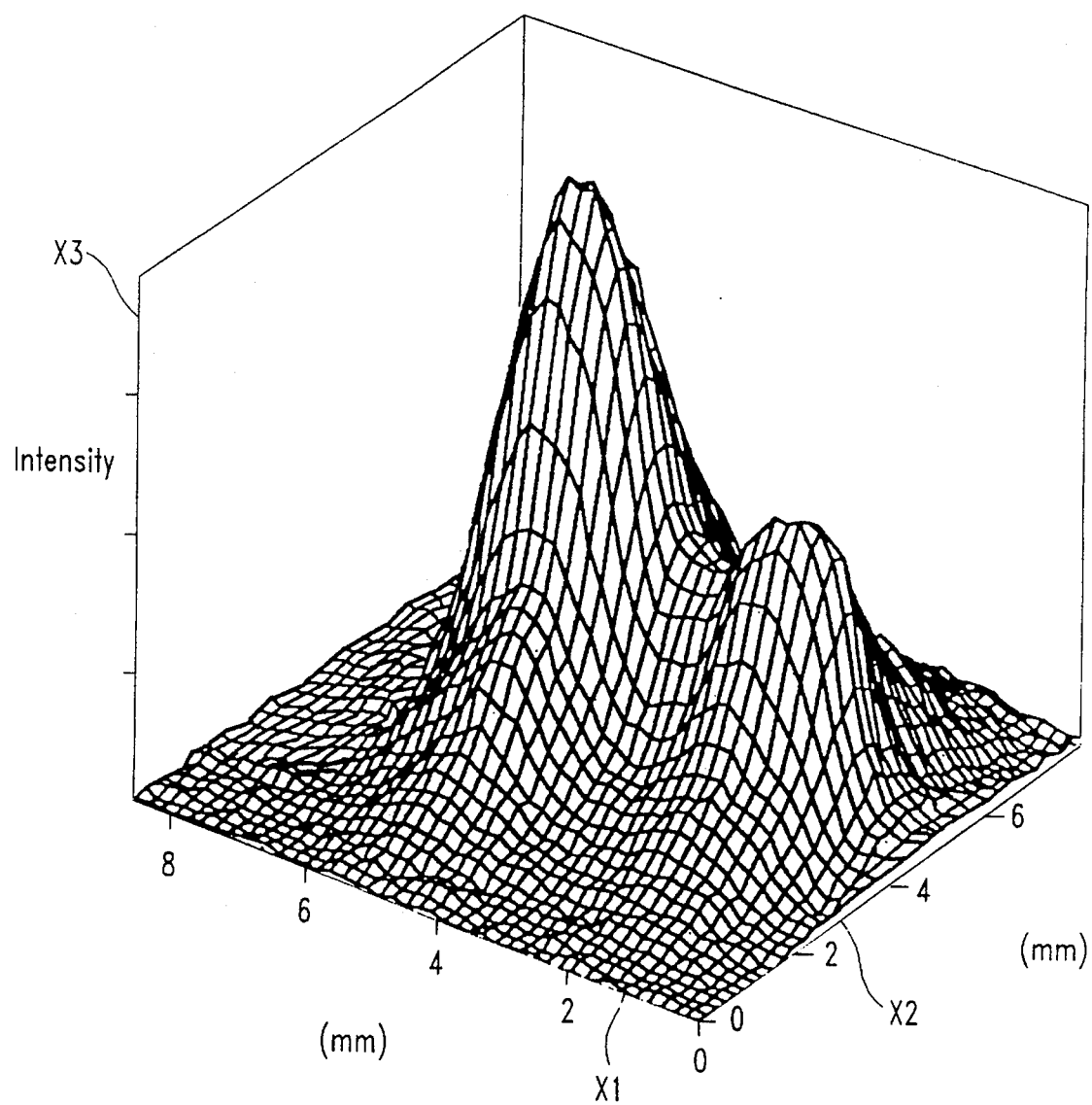
FIG. 3 is a three-dimensional graph useful in understanding the preferred embodiment of the invention.

An example of a typical three-dimensional image of a transverse mode created by computer 45 and displayed on display 46 appears in FIG. 3, which shows a graph having orthogonal axes X1, X2 and X3. The respective axes X1 and X2 represent the column and row coordinates of pixel locations which correspond to z' and x coordinate locations on front surface 22. Axis X3 represents the intensity of the light illuminating the CCD's at each of the pixel locations. As seen in FIG. 3, row and column contour lines connect the light intensity points to graphically illustrate a three-dimensional image of the real-time intensity function and, therefore, the real-time acoustic power of the acoustic wave. Alternatively, real-time images may also be displayed and recorded by replacing CCD array 44, frame grabber 48, computer 45 and display 46 with an instant camera system or projection screen located at the image plane of lens 41. Those skilled in these arts will recognize other techniques for obtaining such real-time images or records.

While the present invention has broad application, a number of attributes thereof make it particularly suitable for imaging low-efficiency acoustic wave devices. As discussed above, the total internal reflection technique of the present invention has improved optical efficiency and good reduction of stray light when compared to conventional geometrical arrangements that use external reflection, transmission and/or partial internal reflection.

Specifically, because of the high optical efficiency of the optical arrangement of the present invention, low-cost, high-reliability, low-power lasers, such as HeNe lasers, may be used as the light source. Also, stray light suppression in optical imaging system 30 is superior to what is generally found in prior art systems that employ external reflection and/or transmission because in the present system much of the stray light directed from surface irregularities on the prism's entrance face 34 will propagate at angles less than the critical angle and, therefore, be refracted out of front surface 22 and not into the focus plane. Further, expanded laser beam 31 enables system 30 to perform large-area imaging in real time such that the entire resonator 20 may be imaged including cavity 29, transducers 23 and 24, reflectors 27 and 28, deposited metal layer 19 and bus bars connecting input source 25 and load 26, and other elements and areas on front surface 22.

Additionally, in the present invention, front surface 22 is accessible for direct mechanical, thermal and other probing without interfering with the imaging process. The total internal reflection technique of the present invention has special utility with STW devices because deposited metal layer 19 makes it impossible to image the acoustic modes using external reflection or transmission imaging. Of course, the total internal reflection imaging technique of the present invention is unaffected by the presence of metal layer 19.

Yet further, because the back surface of resonator 20 is refractive-index matched to prism 33 via refractive index matching fluid 37, the back surface of resonator 20 only needs to be lapped, not polished as is usually necessary in transmission imaging systems. Still further, because the angular separation between undiffracted beam B0 and diffracted beams −B1 and +B1 increases with the reciprocal of the cosine of the angle of incidence of laser beam 31 (about forty-five degrees), such angular separation in system 30 can be as much as forty percent greater than what is possible in transmission systems which usually employ laser beams with normal incidence angles. The resulting large angular beam separation facilitates effective spatial filtering, via spatial filter 42, of the high-intensity undiffracted component B0. Also, if the high intensity undiffracted component B0 is allowed to pass through the spatial filter and instead is attenuated by, for example, neutral density filtering, both the undiffracted image of the entire device and the diffracted image of the acoustic mode on or beneath the front surface may be simultaneously imaged. In addition, the large incidence angles of the present invention assure that any phase modulation superimposed on the incident wavefront of laser beam 31 by the surface wave distortions of front surface 22 cannot be effectively canceled by the photoelastic strain modulation, as occurs in other imaging systems.

It should be understood that the foregoing disclosure relates to only preferred embodiments of the invention and that numerous modifications or alterations may be made therein without departing from the spirit and the scope of the invention as set forth in the appended claims.

What is claimed is:

1. An acoustic wave imaging apparatus comprising:

a device having a member with a back surface and a front surface capable of supporting acoustic waves;

optical means for directing a collimated beam of light into said member through said back surface toward said front surface at an angle larger than the critical angle of said member to cause substantially total internal reflection of said collimated beam of light by said front surface;

means for launching acoustic waves in said member for diffracting said beam of light into a plurality of components;

focusing means, having an image plane, for focusing at least one of said components onto said image plane; and display means located at said image plane for generating real-time images of said at least one of said components.

2. The apparatus of claim 1 wherein said member is a piezoelectric crystal.

3. The apparatus of claim 2 wherein said device is a surface acoustic wave device and said means for launching acoustic waves includes an electromechanical transducer mounted on said front surface.

4. The apparatus of claim 2 wherein said device is a surface transverse wave device and said means for launching acoustic waves includes an electromechanical transducer and a metal layer mounted on said front surface.

5. The apparatus of claim 2 wherein said optical means includes a large-beam laser means for illuminating substantially all of the region supporting said acoustic wave.

6. The apparatus of claim 5 wherein said optical means includes an optical prism with a refractive index matching face contacting said back surface.

7. The apparatus of claim 6 wherein said prism further has an entrance face and an exit face oriented orthogonal to each other and at a forty-five degree angle with respect to said refractive index matching face.

8. The apparatus of claim 7 wherein said optical means directs said collimated beam of light normal to said entrance face and at a forty-five degree angle to said front surface.

9. The apparatus of claim 8 wherein said focusing means comprises a focusing lens having a focal plane, and further including a spatial filter mounted at said focal plane with means for selectively passing said at least one of said components and blocking the other of said components.

10. The apparatus of claim 9 wherein said display means includes means for generating and displaying in real time a three-dimensional spatial image of the intensity of said at least one of said components.

11. The apparatus of claim 10 wherein said display means further includes a charge coupled array mounted at said image plane, a frame grabber connected to said charge coupled array, a computer connected to said frame grabber and a real-time display connected to said computer.

12. An acoustic wave imaging method comprising:

mounting a device with a member capable of supporting acoustic waves and having with a back surface and a front surface;

directing a collimated beam of light into said member through said back surface and incident with said front surface at an angle larger than the critical angle of said member to cause substantially total internal reflection of said collimated beam of light by said front surface;

launching acoustic waves in said member to diffract said beam of light into a plurality of components upon said total internal reflection;

focusing at least one of said components onto said image plane; and generating real-time images of said at least one of said components.

13. The method of claim 12 wherein said directing step includes illuminating substantially all of the region in said member supporting said acoustic waves with a large-diameter laser beam.

14. The method of claim 13 wherein said directing step includes providing an optical means having an optical prism with an entrance face and an exit face oriented orthogonal to each other and at a forty-five degree angle with respect to a refractive index matching face that contacts said back surface, and directing said collimated beam of light normal to said entrance face and at a forty-five degree angle with respect to said front surface.

15. The method of claim 14 wherein said focusing step includes providing a focusing lens having a focal plane and mounting a spatial filter at said focal plane, and wherein said spatial filter passes said at least one of said components and blocks the other of said components.

16. The method of claim 15 wherein said display step includes generating and displaying in real time a three-dimensional spatial image of the intensity of said at least one of said components.

* * * * *